United States Patent
Brecht

(10) Patent No.: US 10,624,840 B2
(45) Date of Patent: Apr. 21, 2020

(54) METHOD FOR PERFORMING COSMETIC SURGICAL PROCEDURES USING TUMESCENT ANESTHESIA AND ORAL SEDATION

(71) Applicant: Kristine Brecht, Burien, WA (US)

(72) Inventor: Kristine Brecht, Burien, WA (US)

( * ) Notice: Subject to any disclaimer, the term of this patent is extended or adjusted under 35 U.S.C. 154(b) by 0 days.

(21) Appl. No.: 16/051,383

(22) Filed: Jul. 31, 2018

(65) Prior Publication Data
US 2019/0038549 A1 Feb. 7, 2019

Related U.S. Application Data

(60) Provisional application No. 62/542,141, filed on Aug. 7, 2017.

(51) Int. Cl.

| | | |
|---|---|---|
| *A61K 9/00* | (2006.01) | |
| *A61K 31/137* | (2006.01) | |
| *A61K 45/06* | (2006.01) | |
| *A61K 31/167* | (2006.01) | |
| *A61K 8/00* | (2006.01) | |
| *A61K 31/485* | (2006.01) | |
| *A61K 31/495* | (2006.01) | |
| *A61K 31/437* | (2006.01) | |
| *A61K 31/5513* | (2006.01) | |
| *A61K 31/5415* | (2006.01) | |
| *A61K 31/5517* | (2006.01) | |
| *A61K 9/08* | (2006.01) | |
| *A61K 47/02* | (2006.01) | |
| *A61K 31/4164* | (2006.01) | |

(52) U.S. Cl.
CPC .............. *A61K 9/0019* (2013.01); *A61K 8/00* (2013.01); *A61K 31/137* (2013.01); *A61K 31/167* (2013.01); *A61K 31/437* (2013.01); *A61K 31/485* (2013.01); *A61K 31/495* (2013.01); *A61K 31/5415* (2013.01); *A61K 31/5513* (2013.01); *A61K 31/5517* (2013.01); *A61K 45/06* (2013.01); *A61K 9/08* (2013.01); *A61K 31/4164* (2013.01); *A61K 47/02* (2013.01)

(58) Field of Classification Search
CPC ...... A61K 9/0019; A61K 9/08; A61K 31/137; A61K 31/167; A61K 31/4164; A61K 31/5517; A61K 31/437; A61K 31/485; A61K 31/495; A61K 31/5513; A61K 31/5415; A61K 45/06; A61K 47/02; A61K 8/00; A61K 2300/00
See application file for complete search history.

(56) References Cited

U.S. PATENT DOCUMENTS

| | | |
|---|---|---|
| 6,921,541 B2 | 7/2005 | Chasin |
| 2009/0048237 A1 | 2/2009 | Palmer et al. |
| 2017/0100331 A1 | 4/2017 | Klein |

OTHER PUBLICATIONS

Salkind et al., "Antibiotic Prophylaxis to Prevent Surgical Site Infections" In American Famili Physician, vol. 83, No. 5, Mar. 1, 2011, pp. 585-590.*
Hsu et al., "Infection Prophylaxis Update" in Seminars in Plastic Surgery, vol. 20, No. 4, 2006.*
Grunebaum et al., "Perioperative Antibiotic Usage by Facial Plastic Surgeons" in Arch, JAMA Facial Plast Surg vol. 8, Mar./ Apr. 2006.*
1727_001.pdf Dashkovsky et al. "Preemptive analgesia with controlled-release oxycodone is successful in prevention of post-inguinal herniorrhaphy pain" in Journal of Ambulatory Surgery (11) (2004) pp. 11-13.*
Masters, P.A. et al. "Trimethoprim-Sulfamethoxazole Revisited." Arch. Intern. Med., 2003, 163: pp. 402-410.
Reichart, B. et al. "Surgical Management of Heart-Lung Transplantation." Ann. Thorac. Surg., 1990, 49: pp. 333-340.

\* cited by examiner

*Primary Examiner* — Blessing M Fubara
(74) *Attorney, Agent, or Firm* — Wooshik Shim; John D. Houvener; Bold IP, PLLC

(57) ABSTRACT

A method for anesthetizing a patient undergoing a cosmetic surgical procedure comprising: providing an antibiotic medication at least from about 12 hours to about 24 hours prior to the cosmetic surgical procedure; providing a first dosage of oxycodone and a first dosage of promethazine to be taken by the patient prior to arrival at a surgical facility where the cosmetic surgical procedure is to occur; and providing a dosage of lorazepam, a dosage of zolpidem, and a dosage of hydroxyzine just prior to the cosmetic surgical procedure, wherein the zolpidem comprises a dosage of AMBIEN. In one embodiment, the method further comprises: preparing an anesthetizing solution comprising lidocaine, epinephrine, and sodium bicarbonate; and infiltrating the anesthetizing solution in a targeted area of the patient. In another embodiment, the method further comprises: providing one or more reversing agents to the patient after the cosmetic surgical procedure.

20 Claims, 3 Drawing Sheets

METHOD FOR PERFORMING COSMETIC SURGICAL PROCEDURES USING TUMESCENT ANESTHESIA AND ORAL SEDATION

CROSS-REFERENCE TO RELATED APPLICATIONS

This application claims priority to U.S. Provisional Application No. 62/542,141 filed Aug. 7, 2017.

FIELD OF THE INVENTION

The field of invention generally relates to a method of administering anesthesia to a patient prior to and during a variety of cosmetic surgical procedures. More specifically, the field of invention relates to techniques and procedures for a patient to undergo cosmetic surgical procedures, including tumescent liposuction, without requiring the use of general anesthesia or intravenous (IV) administered anesthesia, and to provide a more pleasant experience that reduces the anxiety of a patient prior to and while undergoing surgery, as well as provides optimal results post-surgery.

BACKGROUND OF THE INVENTION

Cosmetic surgery encompasses a number of techniques and surgical procedures that focus on enhancing and improving the aesthetic appeal of one or more parts of the body. Beneficially, cosmetic surgical procedures may also provide a number of positive benefits for the overall health and well-being of a patient. While the terms plastic surgery and cosmetic surgery are often used interchangeably by patients, there are some important technical differences. While both cosmetic surgery and plastic surgery deal with improving a patient's body, the overarching training, background certification, and even goals for patient outcomes are not always the same. Particularly, plastic surgery is defined as a surgical specialty dedicated to reconstruction of facial and body defects due to birth disorders, trauma, burns, and disease. Plastic surgery intends to correct dysfunctional areas of the body to achieve a more "normal" function and appearance and is thus reconstructive in nature. On the other hand, the procedures, techniques, and principles of cosmetic surgery are mostly focused on enhancing a patient's appearance. Thus, the key goals for cosmetic surgery are to improving aesthetic appeal, symmetry, and proportion of areas of the human body. Further, cosmetic surgery is usually elective, because the treated areas are usually functioning properly.

Cosmetic surgery is a surgery specialty practiced by doctors from a variety of medical fields, including, but not limited to, plastic surgeons. To become well-versed in commonly sought cosmetic surgical procedures, additional training and exposure may be required by any physician, including a plastic surgeon. While some cosmetic surgical procedures are included in the plastic surgeon's medical residency program, it is highly recommended that anyone who is performing any cosmetic surgical procedure go above and beyond the minimum level of training to ensure they have experience in performing all cosmetic surgery procedures of the face, neck, breast, and body.

Despite the above clarification of some differences between plastic surgery and cosmetic surgery, it is noted that patients will often seek out either a plastic surgeon and/or a physician who specializes in cosmetic surgery based on their extensive training to enhance and improve the aesthetic appearance of one or more body parts of concern to the patient. For simplification of the present description, cosmetic surgery will be referred to throughout the remainder of the description as including certain elective, aesthetic enhancement surgical procedures that may be performed by any qualified, licensed physician, including cosmetic surgeons or plastic surgeons, but most preferably, by very experienced, highly trained physicians, including cosmetic surgeons and/or plastic surgeons, who focus on providing their medical services with the highest possible levels of patient care and patient safety.

Cosmetic surgery may be performed on all areas of the body, with the focus on enhancing and improving the aesthetic appearance, symmetry, and proportionality of these various parts of the human body. The scope of work included in cosmetic surgical procedures may relate to breast enhancement, facial surgery, body contouring, and/or skin rejuvenation. In terms of breast enhancement, cosmetic surgeons may be sought out by a patient to perform breast lifts, breast augmentation (to increase the size of the breast), or even breast reductions to reduce the size of overly large breasts. Additionally, cosmetic surgeons are well known for providing body contouring surgical procedures such as arm lift (brachioplasty), buttock enhancement, tummy tucks (abdominoplasty) and liposuction. Further, facial rejuvenation is frequently sought out by patients who may elect to undergo a facelift, facial implant and/or eyelid lift, neck lift, or brow lift to reduce the effects of age, such as sagging of the skin, wrinkles, and other side effects of ageing to one's face. Other commonly desired cosmetic surgical procedures may include facial contouring surgical procedures such as rhinoplasty, chin, or cheek enhancement.

It is important to note that these cosmetic surgical procedures require a great deal of skill and expertise on the part of a cosmetic surgeon who must train extensively for many years. Extensive training in cosmetic surgery and patient care is required not only so that the cosmetic surgeon can hone his or her skills in shaping and enhancing parts of the body, but also because there is a very real risk for any number of life-threatening conditions to develop by virtue of the nature of surgery itself and also as a result of the techniques used. For example, there is a serious risk of infection, excessive blood loss, respiratory complications, and/or cardiac arrest occurring while a patient undergoes one or more cosmetic surgical procedures. Therefore, it is important for a cosmetic surgeon to be very mindful and well-versed in all the proper measures to avoid and/or mitigate any such negative health conditions from developing during surgery. Over the years a number of techniques have been developed to ensure the safety and well-being of a patient undergoing a cosmetic surgical procedure, but complications do still arise, and it is important to remain vigilant of these risks.

Ultimately, cosmetic surgeons are aware that their patients seek them out to achieve aesthetic rejuvenation and to improve their physical appearance. In addition to the improvements in physical appearance, it is well-documented that additional positive side-effects to cosmetic surgery include 1) a vast improvement in how patients feel about themselves 2) increased opportunities in their personal and professional lives, and often 3) improved mental health. Further, while many of the above-mentioned procedures aim to improve the aesthetical appearance of a body part, there may also be a number of physical health benefits from the cosmetic surgical procedure as well. For example, rhinoplasty is a nose shaping surgery performed on a patient that reshapes the patient's nose to improve the overall shape, but also, has the added benefit of improving a patient's ability to breath from their nose. Likewise, after undergoing a breast reduction, a patient is relieved of a great deal of back and neck pain from the excess weight and size of the breasts, and also see an improvement in the symmetry of their overall body profile.

It is no wonder that over 15 million cosmetic surgical procedures have been performed in America alone in recent years. Patients are eager to improve their physical appearance, which is of critical importance. Nevertheless, for many, there does exist a great deal of anxiety associated with the thought of undergoing cosmetic surgery. Additionally, the prospect of being anesthetized and the possible risks and harmful after-effects of various forms of anesthesia, especially general anesthesia, also greatly contributes to the patient's anxiety.

Anesthesia enables the painless performance of medical procedures that would otherwise cause severe or intolerable pain. A patient who is under the effects of anesthetic drugs is referred to as being anesthetized. More specifically, in the practice of medicine, and especially surgery, anesthesia is a state of temporary induced loss of sensation or awareness. In some cases, anesthesia may include analgesia (relief from or prevention of pain), paralysis (muscle relaxation), amnesia (loss of memory), or unconsciousness, particularly when general anesthesia is used.

For purposes of simplification in the present description, a broad overview of several categories of anesthesia is provided. These categories include general anesthesia, epidural/spinal anesthesia, moderate sedation, monitored anesthesia care (MAC), regional anesthesia, and local anesthesia. General anesthesia is associated with a deep sedation, normally administered intravenously (IV) or inhaled. General anesthesia suppresses central nervous system activity and results in unconsciousness and total lack of sensation. Epidural and spinal anesthesia can be used for most surgeries below the belly button, and are frequently used for labor, cesareans, surgeries of the colon and gastrointestinal tract, gynecologic and urologic surgeries. Moderate sedation suppresses the central nervous system to a lesser degree, inhibiting both anxiety and the creation of long-term memories, without resulting in unconsciousness. Monitored anesthesia care (MAC) is the intravenous administration of mild sedatives to help a patient relax and to relieve anxiety during procedures that do not require general anesthesia.

Regional anesthesia and local anesthesia both block transmission of nerve impulses between a targeted part of the body and the central nervous system, causing loss of sensation in the targeted body part. A patient under regional or local anesthesia remains conscious, unless sedation is administered at the same time. Regional anesthesia involves administration of a regional block that is directed at the trunk of a nerve and affects all the branches of the nerve that comes from that trunk. Local anesthesia is injected in a particular area and blocks only where injected, not father down the branches of the nerve.

Traditionally, general anesthesia has been the preferred method by many surgeons for anesthetizing patients undergoing cosmetic surgery. There are both major and minor risks of anesthesia, but particularly so, for general anesthesia where a patient is put in a state of unconsciousness and paralysis. An extreme risk complication as a result of the medicines administered for general anesthesia includes mortality (i.e. death of a patient) and morbidity, which are diseases or disorders that develop as a result of the general anesthesia. For example, surgeons are always aware of the possibility of myocardial infarction (heart attack) and/or cardiac arrest, lung infections and/or pneumonia, pulmonary embolism, renal failure/insufficiency, as well as postoperative cognitive dysfunction occurring responsive to the general anesthesia and as a result of a disorder, a patient may have a severe change in blood pressure, excessive speeding up or slowing down of the heart rate, and also may develop in some rare cases, malignant hyperthermia, where the patient develops a dangerously high temperature that must be reversed.

The risk of deep vein thrombosis (DVT) occurring during cosmetic surgical procedures is always present, particularly in procedures such as face lifts, abdominoplasty (ex. tummy tuck surgery), and especially lower body surgery, and particularly so, when the patient spends longer periods being under general anesthesia. DVT is a condition where a blood clot forms in a deep vein in the body. Blood clots occur when blood thickens and clumps together. Most deep vein blood clots occur in the lower leg or thigh, but they can also occur in other parts of the body. A blood clot in a deep vein can break off and travel through the bloodstream. The loose clot is called an embolus, and it can travel to an artery in the lungs and block blood flow. This condition is called pulmonary embolism (PE), which is a very serious, life-threatening condition, as it can damage the lungs and other organs in the body and cause death.

Due to all these serious risks, only certified anesthesiologists are allowed to administer general anesthesia. Therefore, during cosmetic surgical procedures where the surgeon has determined to administer general anesthesia to a patient, a certified anesthesiologist is responsible for providing the correct dosages and drugs to induce deep sedation and unconsciousness and must be present the entire time the cosmetic surgical procedure is taking place in the operating room. Further, patients under general anesthesia must undergo continuous physiological monitoring to ensure safety in view of all of the risk of complications.

When a patient is under general anesthesia, the patient cannot reliably breathe on their own and also cannot respond to commands. Accordingly, to control breathing when under general anesthesia, patients are intubated and a breathing tube is inserted down the patient's windpipe. The patient must then be attached to a ventilator or other breathing device to ensure that the patient is breathing. The intubation process must be performed very carefully and requires skill to avoid tearing the vocal cords, damaging the airway, perforating the trachea, or accidentally passing the breathing tube through the esophagus and not the trachea, which means that the air is not being delivered to the lungs where it is needed. It is very common for patients to report a sore throat after waking up from general anesthesia due to the intubation, which is a potentially risky technique and requires great skill.

In addition to all of these major risks associated with general anesthesia, there are also what are known as minor risks that are not life-threatening, but that are no less uncomfortable for the patient. The negative side-effects of being under general anesthesia, and these minor risks, include postoperative nausea and vomiting and hospital readmission, as well as urinary retention and constipation, which may be particularly painful and uncomfortable after a patient has undergone a procedure such as a tummy tuck surgery. More common anesthesia risks include waking up confused and disoriented, and shivering. A less common complication is anesthesia awareness, or waking up in the middle of surgery.

Further, the use of an intravenous (IV) sedation during cosmetic surgery to administer anesthesia also presents a number of risks that should not be overlooked. The risks associated with the use of IV sedation during cosmetic surgery include respiratory depression, cardiac depression, stress to a patient from putting in an IV, infiltrated IV, thrombosis of the vein that the IV is located in, as well as thrombophlebitis to name a few of the major concerns. Therefore, the use of IV sedation in lieu of general anesthesia also presents a wide variety of potential complications and concerns that must be closely monitored during the surgical procedure.

Currently there are a number of solutions for surgery anesthesia. As noted above, cosmetic surgeons usually opt for general anesthesia so as to ensure that their patients are in a deep sedation and unlikely to wake up or feel pain. However, Dr. Jeffrey Klein, a dermatologic surgeon, based in Orange County, Calif., is credited with being the inventor of tumescent local anesthesia and tumescent liposuction, which uses local anesthesia during liposuction. Liposuction is the most commonly performed cosmetic procedure in the United States, and elsewhere. It is also referred to as liposculpture or lipoplasty, and is performed by cosmetic surgeons to reduce unwanted, fatty deposits on the body. Most commonly, liposuction is used on the abdomen, thighs, buttocks, neck, chin, upper and backs of the arms, calves, and back.

During liposuction, the fat is removed through a hollow instrument known as a cannula, which is inserted under the skin. A powerful, high-pressure vacuum, which acts as a suction device, is applied to the cannula. Through small incisions, the cannula is inserted into fatty areas between the skin and muscle where the cannula removes excess fat either using a suction pump or a syringe. The effects of liposuction are meant to include a smoother, improved body contour and permanent removal of fat from an area of the body.

In the past, liposuction required blood transfusions because blood loss found in the aspirate was so significant. Further, liposuction was most often performed while the patient was under general anesthesia and asleep. Dr. Jeffrey Klein is well-known for his development and use of tumescent liposuction, which has allowed liposuction to be performed using infiltration of large volumes of tumescent solution during liposuction. Since its inception, liposuction performed with the tumescent technique has had an excellent safety profile.

Tumescent liposuction is a specialized technique of performing liposuction that includes providing local anesthesia in the form of lidocaine mixed with a small amount of epinephrine to large volumes of subcutaneous fat, which thus permits liposuction. Lidocaine, also known as xylocaine and lignocaine, is a medication used to numb tissue in a specific area and can also be used as a local nerve block or local anesthetic. In the tumescent technique for liposuction surgery, large volumes of a diluted solution of lidocaine is mixed with a small amount of epinephrine. Tumescence refers to anything that is swollen and firm. and when used in surgery is a type of infiltration technique used to swell up the fat cells in the targeted area. During tumescent liposuction, the medical provider injects subcutaneously the special solution of salt solution, lidocaine, and epinephrine into the layer of fat. Relatively large volumes (ex. <4 L or more of the solution) are injected ahead of the cannula. The solution swells the fat cells making them easier to isolate and remove. The solution also shrinks blood vessels as a result of the epinephrine, which is a vasoconstrictor. The solution further helps to ease the patient's discomfort because it contains the local anesthesia (i.e. lidocaine) without the risks associated with the general anesthesia. The lidocaine solution is deposited exactly along the eventual pathway of the liposuction cannula that is used to break up and suck up fat from a part of the body.

As noted above, Dr. Klein's tumescent liposuction procedure is highly recognized as being an improved way of performing liposuction. Tumescent liposuction is known for offering several advantages. A primary benefit of the tumescent liposuction in view of traditional methods of performing liposuction is that there is significantly less blood loss that occurs during the fat suction procedure. Nevertheless, Dr. Klein is known for being conservative in terms of the amount of lidocaine recommended during the tumescent liposuction procedure. The traditional way of preforming tumescent liposuction using Dr. Klein's techniques involves a recommended upper limit of 35 milligram (mg) of lidocaine per kilogram (kg) of bodyweight using the diluted solution noted above. Notably, in U.S. Patent No. 2017/0100331, Dr. Klein recommends 28 mg/kg of lidocaine for infiltration of local anesthesia. This may be particularly to avoid significant risks associated with lidocaine toxicity. While generally safe, lidocaine toxicity can be a result of exceeding a maximum safe dosage and may result in circumoral numbness, facial tingling, restlessness, vertigo, tinnitus, slurred speech, and tonic-clonic seizures, and other symptoms of toxicity. Further, Dr. Klein may not recommend using higher concentrations of lidocaine, because he is also known for utilizing IV sedation in combination with the tumescent anesthesia. It is reported that the Klein method involves IV administration of anti-anxiety medications, such as diazepam, during his tumescent liposuction procedures, whereby he administers some form of sedation through an intravenous (IV) catheter filled with the diazepam and used to sedate the patient. Thus, the use of IV sedation is a common occurrence with conventional methods of tumescent anesthesia in cosmetic surgery, including when liposuction is performed, even though there are still many risks and potential problems that may arise because of the use of IV sedation (e.g. respiratory depression, cardiac depression, stress to a patient from putting in an IV, infiltrated IV, thrombosis of the vein that the IV is located in, as well as thrombophlebitis).

Of primary importance is the need to address a patient's anxiety and distress prior to and during a cosmetic surgical procedure. While there are some existing publications that describe combining anesthesia with other agents for various reasons, some of which may have an effect on the anxiety of the patient, these publications are still deficient for many reasons. For example, U.S. Pat. No. 6,921,541 describes a system and method of combination of an augmenting agent and an anesthetizing agent for inducing sustained regional local anesthesia in a patient to prolong the duration of the local anesthesia for a time period longer than that obtainable from the substrate without the augmenting agent. Further, U.S. Patent Publication No. 2009/0048237 (the '237 Publication) describes using oral medications comprising formulations effective for induction of procedural sedation and analgesia (the inability to feel pain), for example prior to induction of general anesthesia. The dosage forms comprise the combination of a drug typically used to treat anxiety, including a drug of the benzodiazepine class, such as triazolam, and an analgesic drug, such as sufentanil, delivered by the oral transmucosal route in a single dosage form. In the '237 Publication, the goal is to effect procedural sedation and analgesia using oral medication during or prior to general anesthesia. However, lacking from either of these patent publications is any utilization of tumescent anesthesia that may also have a number of positive benefits for a patient undergoing a cosmetic surgical procedure and thus fails to encompass a complete approach for maximizing a patient's comfort and reducing any pain or anxiety related to an operation.

There are many conventional pre-operation (pre-op) instructions given to a patient prior to undergoing a cosmetic surgical procedure, including many instructions that require a significant change in their routine starting from the day before the surgery is scheduled to occur. These sudden changes to a patient's routine contributes to the anxious psychological state of the patient prior to surgery. For example, most patients are instructed to fast and are forbidden from ingesting any food or drink (other than water) anywhere from 4-12 hours prior to having a surgical procedure performed. Further, to avoid any possible complication with anesthesia, particularly general anesthesia, patients may be prohibited from taking their regular medicines prior to surgery. When these changes in a patient's routine are compounded with the concerns regarding the risks of being anesthetized using general anesthesia, it is no wonder that a patient may not be in a calm state prior to surgery and may feel a high level of stress and anxiety.

Therefore, there currently exists a need in the industry for a process that allows for a more pleasant, comfortable experience for a patient undergoing one or more cosmetic surgical procedures.

SUMMARY OF THE INVENTION

The disclosed method is unique when compared with other known processes and solutions in that it allows for a quick recovery time, greater patient comfort prior to and during surgery, and focuses on relieving patient anxiety prior to surgery as well. The disclosed method is further unique in that it is different in methodology from other conventionally known or accepted processes or solutions. More specifically, the method described herein may encompass a method for preparing a patient for a cosmetic surgical procedure and providing medications that have the effect of sedating, relieving anxiety, and preventing the patient from feeling pain prior to and during surgery without using either general anesthesia or IV sedation during the cosmetic surgical procedure. Further, the method described herein may encompass steps for utilizing tumescent anesthesia for any type of cosmetic surgical procedure, including during liposuction. In addition to the above, a method for performing liposuction using tumescence, and a combination of water-assisted liposuction, power-assisted liposuction, and ultrasound assisted liposuction for optimal fat removal and contouring results is also described in the present description.

In one aspect, a method for preparing a patient for surgery with the intent to relieve anxiety and prevent the patient from feeling pain prior to and during surgery may include the oral administration of medications including: (1) an antibiotic medication taken at least 24 hours before surgery and optionally a sedative to prevent insomnia; (2) an anxiolysis (e.g. promezathine) and analgesic agent (e.g. oxycodone) taken the day of surgery no later than two hours prior to surgery and preferably prior to the patient's arrival at the operating center; and (3) subsequent to taking the anxiolysis and analgesic agent, taking an immediate-acting benzodiazepine medication (e.g. lorazepam), a sedative medication (e.g. AMBIEN), and another sedative (e.g. hydroxyzine)(all administered as oral medications). The combination of the above-listed medications has several positive results, including, but not limited to, providing relief from anxiety that is natural for a patient to feel prior to surgery and also providing a moderate level of sedation to both calm the patient and to induce a sense of drowsiness and sleepiness. Further, the combination of medications, in particular, the administration of the oxycodone acts to prevent the patient from feeling pain.

Upon administration of all of these above-listed medications in preparation for surgery, a period of time may be allowed to pass to assess and analyze the level of acceptance and tolerance of the medications by the patients. If, upon analysis, a patient is not sufficiently sedated or also appears overly anxious, the medical care provider may oversee administration of an additional dosage of an oral analgesic agent, such as oxycodone, and an additional dosage of the anxiolytic agent, such as promethazine. The intended effect of the combination of the medications is to provide sedation, relief from anxiety, and prevention of a sense of pain. Further, the combination of the medications is intended to replace the need for general anesthesia or IV administered sedation of a patient during surgery, which as noted above, include a number of potential problems and risks that can affect the wellbeing of a patient. This may include both the physical and psychological stress that is put on the patient due to the use of general anesthesia and IV sedation. Accordingly, it is important that the medical care provider be aware of the receptivity of the patient to the combination of the above-listed medications to ensure that the medicines 1) provide the desired effect and 2) do not produce any unwanted reactions for the patient. Further, prior to any administration of any of the above-listed medicines, a medical care provider should conduct an initial consultation and a preoperative evaluation ("pre-op"), which is discussed in further detail later in the present description.

After a minimal period of time has passed for the combination of above-listed medications to take effect, the physician makes an assessment of the anxiety level, sedation level, and threshold level of pain tolerance of the patient. The above-combination of medications may be modified to include additional levels of sedation if a patient already has a high tolerance for any of the medications noted above and/or a high tolerance for pain.

In accordance with one or more embodiments, a process for preparing a patient prior to surgery without the use of general anesthesia or IV sedation, may continue with providing the patient with a dosage of lorazepam. Further, the physician may provide zolpidem, in the form of a dosage of AMBIEN, which is a Trademark for zolpidem sold by Sanofi-Aventis, U.S. LLC of Bridgewater Township, N.J., and further provide a dosage of hydroxyzine.

As the medications take effect, the patient may begin to feel symptoms such as drowsiness or desire to sleep, as well as a sense of calmness, lack of anxiety, and/or numbness or lack of sensation of pain. The patient may begin to exhibit signs that the medications have taken effect because the patient may begin slurring their speech and/or appears extremely sedated and/or not lucid. Usually, the patient is still also conscious and ambulatory. All of the above-listed combinations of medications may be used as described above to prepare a patient for surgery (e.g. a cosmetic surgical procedure) that is performed without the use of general anesthesia or IV sedation. Thus, the proposed combination of medications replaces the medications and procedures that would be utilized in their absence with general anesthesia. As a result of this process, the patient avoids complications that may arise because of the deep sedation required for general anesthesia as well as the post-operation discomfort that results from the use of general anesthesia, including avoiding the sore throat or complications from intubation, nausea, vomiting, disorientation, and many other post-general anesthesia reactions.

Upon determining that the patient is ready for surgery, the patient may be directed to the operating room. A method in accordance with one or more embodiments may further include a preparation of tumescent local anesthesia to be used while the physician performs one or more cosmetic surgical procedures. A physician may prepare in advance the tumescent local anesthesia solution to be utilized during the cosmetic surgical procedure. In one embodiment, the tumescent local anesthesia solution may include a combination of lidocaine, epinephrine, and sodium bicarbonate that has been diluted in normal saline. Further, an amount of lidocaine in the tumescent local anesthesia solution may be from about 45 mg/kg of body weight to about 55 mg/kg of body weight. Thus, a cosmetic surgical procedure may be performed with the provided combination of medications that provide oral sedation and relief from anxiety for the patient prior to undergoing the cosmetic surgical procedure. Further, the use of tumescent local anesthesia during any cosmetic surgical procedure will further ensure the prevention of pain and discomfort of the patient during the cosmetic surgical procedure without using general anesthesia or IV sedation.

In addition to the utilization of the tumescent local anesthesia to reduce bleeding and effectively remove unwanted fat from a targeted area, the improved method for performing liposuction further includes utilizing water-assisted liposuction, power-assisted liposuction, and ultrasound assisted liposuction. The combination of all of these techniques and procedures may produce the most optimal results for a patient, including significantly improved contouring with minimal lumpiness or sagging of the skin, and further may include a faster post operation recovery for the patient.

In addition, the method may further include using one or more reversing agents to reverse the effects of anti-anxiety medication, analgesic agents, or both, which are administered after the surgery. After reversing agents are administered, patients are more alert from their groggy and sleepy states, such that caregivers will be able to more easily take care of the patients.

The foregoing summary is illustrative only and not intended to be in any way limiting. Other aspects and advantages of the invention will be apparent from the following description and the appended claims.

BRIEF DESCRIPTION OF THE DRAWINGS

The present invention will be described by way of exemplary embodiments, but not limitations, illustrated in the accompanying drawings in which like references denote similar elements, and in which.

DEFINITIONS

Figure 1A:
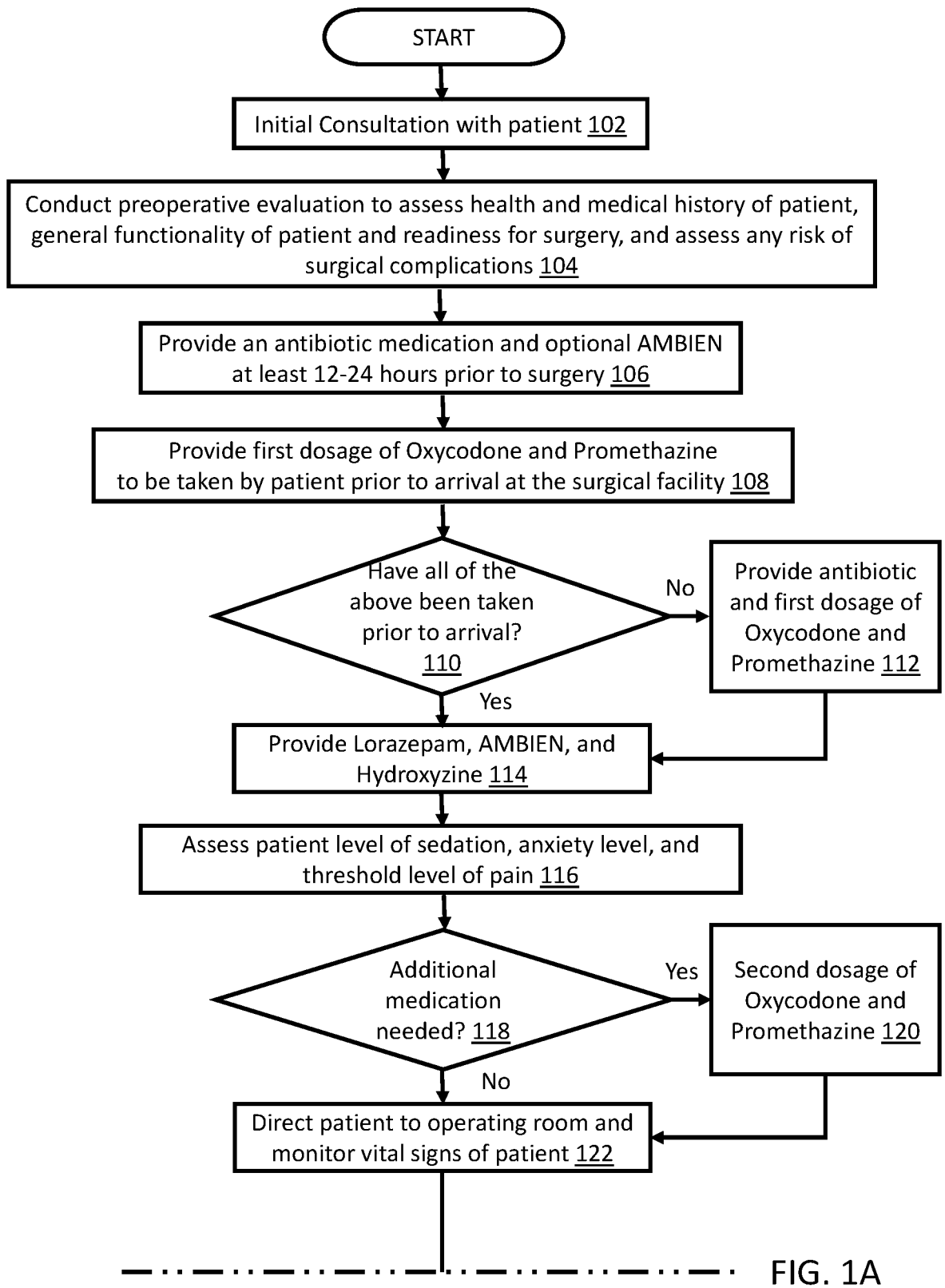
FIG. 1A is a first partial view of a flowchart illustrating a method of treatment of a patient prior to one or more cosmetic surgical procedures in accordance with an illustrative embodiment.

For clarification of terms describing features of one or more embodiments of a method according to the present invention, as claimed herein, particular terms are defined below:

"Surgical facility" may refer to a location for preparing a patient for surgery, and may include, but is not limited to, a hospital-based facility or office based facility.

"Operating room" may refer to a location for performing a cosmetic surgical procedure including an operating room in a surgical facility.

"Surgeon" as used herein may include a licensed physician of one or more medical specializations, including, but not limited to, a specialization in cosmetic surgery and/or plastic surgery.

"Brachioplasty" may also be referred to herein as an arm lift.

"Blepharoplasty" may also be referred to herein as an eyelid lift.

"Forehead lift" may include the performance of a brow lift.

"Rhytidectomy" may also be referred to as a face lift.

"Lower Rhytidectomy" may also be referred to as a neck lift.

"Breast enhancement" treatments may include a breast reduction, breast augmentation, mastopexy, or gynocomastia treatment.

"Breast augmentation" may also be referred to as a breast implant.

"Mastopexy" may also be referred to as a breast lift.

"Gynocomastia" may also be referred to as a treatment for male breast reduction.

"Abdominoplasty" may also be referred to as a tummy tuck.

"Otoplasty" may also be referred to as ear surgery.

"Liposuction", "lipoplasty", "liposculpture suction", "lipectomy" "lino" may be referred to as a procedure for the breaking up and removal of fat from the body via "suction" of the fat.

"Fat Transfer" may include any fat grafting procedure for the transfer of fat from one or more areas of the human body to any other area of the human body, including but not limited to, the breast, buttocks, face, or hands.

"IV sedation" may be used herein as an abbreviation for intravenous sedation.

"Cosmetic surgical procedure" may include, but is not limited to, any surgical procedure to improve the aesthetic appeal including a symmetry and proportionality of any part of the human body for either males or females, including but not limited to, an ear surgery, eyelid surgery, arm lift, brow lift, face lift, neck lift, breast enhancement, including breast implant and breast lift, tummy tuck, liposuction, or fat transfer procedure.

"Tumescence local anesthesia," "tumescent local anesthesia," or "tumescent anesthesia" refers to the use of an anesthetizing solution of lidocaine, epinephrine, and sodium bicarbonate that is injected into a targeted area of the body in advance of and during a cosmetic surgical procedure to cause swelling and firmness of the surgical area for a targeted region of the body.

"Reversing agent" refers to any drug used to reverse the effects of anesthetics, narcotics, or potentially toxic agents.

DETAILED DESCRIPTION

In the Summary above and in this Detailed Description, and in the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined).

In the following detailed description, numerous specific details are set forth in order to provide a more thorough understanding of the one or more embodiments described herein. However, it will be apparent to one of ordinary skill in the art that the invention may be practiced without these specific details. In other instances, well-known features have not been described in detail to avoid unnecessarily complicating the description.

The present disclosure is generally drawn to one or more methods for treatments of sedation and anesthesia of a patient prior to and while undergoing a cosmetic surgical procedure. In particular, one or more embodiments of the method may provide for sedation and anesthetizing targeted areas of a patient's body without the need for general anesthesia or IV sedation. This is particularly unique and a novel method to performing cosmetic surgical procedures, as most cosmetic surgeons favor using general anesthesia and/or IV sedation which present a risk of a variety of complications and discomfort for a patient.

General anesthesia, as noted above, requires that a patient is unconscious and is not able to breathe on his or her own. Rather, a patient is intubated and connected to a breathing machine. Further, there are many major risks associated with general anesthesia, including risk of respiratory and heart related disorders that are serious and life-threatening. At a basic level, patients who have had general anesthesia administered to them may suffer from nausea, vomiting, mild to severe disorientation, constipation, and have a myriad of other symptoms post-operation that are due to the general anesthesia that make the post-operation recovery time that much longer and an uncomfortable experience for the patient.

In addition, the use of general anesthesia at a surgical facility at the time when a cosmetic surgical procedure is scheduled to occur does not address the build-up of anxiety and stress felt by a patient prior to undergoing cosmetic surgery. It is important not to underestimate how intense this sense of anxiety and stress may be for the patient, and it may be one of the key controlling components to the sense of satisfaction that a patient feels about having surgery. Lacking from the usual methods of treating patients is an awareness of and attention to how important it is to provide a sense of anxiety relief and a sense of calmness for the patient prior to surgery. It is a desirable advantage of one or more embodiments of methods provided in the present description that the patient will have a better reaction to the entire process prior to, during, and after undergoing a cosmetic surgical procedure, and is likely to describe the experience as being a pleasant experience.

In accordance with the above, the present description provides an exemplary embodiment of a novel combination of oral medications (e.g. drugs in the form of tablets, capsules, or any other pharmaceutically acceptable carrier known in the art) that address anxiety, pain, and/or sedation of a patient in preparation for any type of cosmetic surgical procedure. Further, the present description includes a novel process for utilizing tumescence as an effective means of anesthetizing the targeted areas of the body prior to surgery and also provides better overall results in terms of the quality of the cosmetic surgical procedure.

Further, the present description provides an exemplary embodiment of a novel process for combining tumescence liposuction with a series of techniques for performing liposuction that includes utilizing water-assisted liposuction, power-assisted liposuction, and ultrasound assisted liposuction. Beneficially, the processes offered in the present description include a number of steps and techniques that may be used to perform one or more cosmetic surgical procedures to enhance a patient's sense of satisfaction, happiness, and comfort level going into a cosmetic surgical procedure and thereafter.

Cosmetic surgical procedures, as used in the present description, may include, but are not limited to, any type of brachioplasty, blepharoplasty, a forehead lift which may also include a brow lift, a rhytidectomy, a lower rhytidectomy, any breast enhancement procedure including a breast reduction, breast augmentation or implant, mastopexy (a.k.a. breast lift), or gynocomastia, an abdominoplasty, a thigh lift, or otoplasty procedure. Further, cosmetic surgical procedures may include liposuction, or liposculpture suction. Additionally, or alternatively, cosmetic surgical procedures may include any type of fat transfer procedure to any part of the body, including face, neck, hands, breast, buttocks, or other part of the body.

As was mentioned above, a brachioplasty may also be referred to in the present description as an arm lift. As used herein, blepharoplasty may also be referred to as an eyelid lift. A rhytidectomy may also be referred to as a face lift and a lower rhytidectomy may also be referred to as a neck lift. Further, a patient may seek out a physician for breast enhancement procedures, which may be any of a breast reduction to reduce the size and/or shape of the breasts, a breast augmentation, or a mastopexy. As used, breast augmentation may also be referred to as a breast implant using any type of implants known in the art of any desirable size. Mastopexy may also be referred to as a breast lift. Further, abdominoplasty, as referred to herein, may also interchangeably be referred to as a tummy tuck. Any of the above procedures may be performed using a number of techniques and procedures as known to a skilled person in the art or as yet to be developed. For purposes of simplification, some details that would be known by one of ordinary skill in performing the above-mentioned procedures have been omitted.

Liposuction (which is also known as "lipoplasty," "liposculpture suction," "lipectomy," or "lipo") may refer to a procedure for the breaking up and removal of fat from the body via "suction" of the fat. Liposuction is one of the most popular cosmetic surgical procedure performed in the U.S. each year. Liposuction is frequently performed as an initial component or part of an underlying procedure for performing many other cosmetic surgical procedures. The liposuction procedure helps to shape and contour a patient's body by removal and/or sculpting of the fat, and further may be a necessary process for performing an arm lift, thigh lift, tummy tuck, or any other type of cosmetic surgical procedure. A patient may choose to have an arm lift when they feel that their arms are too big and also have sagging skin. In such an instance, liposuction is used as part of the arm lift procedure to reduce fat and then the skin may be tightened around the arm to give the arm a more youthful, toned, and improved aesthetic appearance.

The removed fat obtained from a liposuction procedure is also frequently repurposed and injected into another area of the body. "Fat transfer," as used herein, may include any fat grafting procedure for the transfer of fat from one or more areas of the human body to any other area of the human body, including the breast, buttocks, face, or hands. This procedure may be optimal for those who have aging skin and want to provide volume underneath the skin to provide a more youthful, enhanced appearance. Fat transfer procedures may also be used when a patient would like for a certain area of the body to be curvier and/or of a somewhat larger size, including the breasts and buttocks region.

It is preferable that the physician is well-versed and highly knowledgeable in performing cosmetic surgical procedures based on experience and medical training. As noted above, there are major and minor risks to a patient's care, safety, and well-being, and an attending physician who will be performing a cosmetic surgical procedure should be well-aware of any such risks and take all necessary steps to avoid them. Further, for one or more processes described below, it is necessary that the physician is trained in the use of tumescence anesthesia during not only tumescent liposuction, but any type of cosmetic surgical procedure that is performed by the physician. Further, it is necessary for the physician to be trained in the use of various medications (e.g. in tablet, capsule, or any other pharmaceutically acceptable format known in the art) that provide relief from pain, anxiety, and sedation that are further described below and any possible contradictions or harmful reactions that may occur in advance of their prescription to the patient.

Figure 1B:
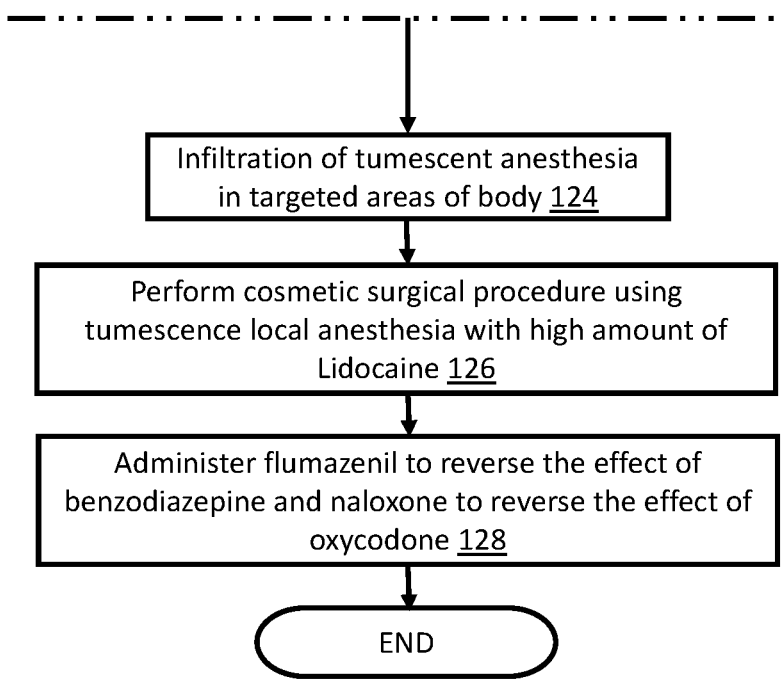
FIG. 1B is a second partial view of a flowchart illustrating a method of treatment of a patient prior to one or more cosmetic surgical procedures in accordance with an illustrative embodiment.

Turning to FIGS. 1A-1B, FIGS. 1A-1B show a flowchart illustrating a method of treatment of a patient, including a method for a medical provider to prepare a patient prior to one or more cosmetic surgical procedures and to perform one or more cosmetic surgical procedures in accordance with an illustrative embodiment. To begin with, at step 102, the process begins with the initial consultation between the cosmetic surgeon and the patient. At the initial consultation, the physician obtains any relevant information about targeted areas of the body that are of concern to the patient and may recommend which cosmetic surgical procedures are the most effective and suitable for the patient to address these concerns. Next, at step 104, the physician may conduct a preoperative evaluation of the patient to assess the health and medical history of the patient. This preoperative evaluation should include the general functionality of the patient and whether the patient is a good candidate for surgery or not. For example, the best candidates are those who are generally healthy, and in particular, are non-smokers. Importantly, the preoperative evaluation provides the physician with the opportunity to obtain all the pertinent data related to the unique medical history of the patient. The physician needs to be aware of the risk of surgical complications arising as a result of the patient's health and any existing conditions that may contribute to surgical complications. Surgical morbidity and mortality generally fall into one of three categories: cardiac, respiratory, and infectious complications. From the initial consultation, the medical health care provider should obtain information to help predict any such complications, including obtaining information about the patient's health history, any medications or supplements used by the patient, lifestyle habits including drinking and smoking habits, and whether the patient uses any narcotics, known conditions, disorders, or diseases of the patient. The initial consultation should also include a physical examination of the patient and documentation of relevant patient vital signs and standard laboratory tests, including blood testing. The information obtained from the initial consultation and pre-op may allow the physician to make a determination of the patient's functional capacity and to determine whether there are any risk factors for cardiac, pulmonary, and infectious complications to occur during surgery.

All of the above are valuable parts of the preoperative evaluation. Additional laboratory studies obtained prior to the operation may be helpful to monitor known disease states. Ultimately, the medical health care provider, prior to administration of the combination of medications described herein, will want to determine the likelihood of any unwanted reactions occurring as a result of using these medications and also to avoid the risk of heart or lung complications based on the unique health of the patient.

The purpose of the preoperative evaluation is to clear patients for elective surgery, to evaluate, and, if necessary, implement measures to prepare higher risk patients for surgery. Preoperative outpatient medical evaluation can decrease the length of hospital stay as well as minimize postponed or cancelled surgeries. To effectively provide this consultative service, the physician should understand the risk associated with the particular type of surgery planned and relate this risk to the patient's underlying acute and chronic medical problems. The complete consultation should include recommendations for evaluation and treatment to minimize the preoperative risk.

Following a thorough preoperative evaluation and a determination by the cosmetic surgeon that the patient is cleared to proceed with one or more cosmetic surgical procedures, the cosmetic surgeon may begin preparing the patient for surgery, including providing general preoperative guidelines that are known in the art. The physician may provide any guidelines for nutritional changes or to stop taking any medicines that may interfere with the combination of medications listed below.

A novel element of a method for readying the patient for a cosmetic surgical procedure that is provided in the present description is that the cosmetic surgeon takes steps to alleviate any pain, anxiety, or risk of infection during surgery by providing relevant medications for a patient to take before a patient arrives at a surgical facility. Accordingly, at step 106, a cosmetic surgeon may have prescribed an antibiotic medication to be taken by the patient at least 12-24 hours prior to a scheduled time for performing a cosmetic surgical procedure. The antibiotic medication may be used to treat a wide variety of bacterial infections, including skin infections and infection of wounds. The antibiotic medication may be beneficially used to prevent bacterial infections from occurring during the cosmetic surgical procedure to be performed the next day. It is noted that providing an antibiotic medication the evening before a surgery is to take place is not considered a routine or ordinary procedure. Rather, the conventional approach is to provide an antibiotic shortly before the cosmetic surgical procedure is to occur.

Further, as shown at step 106 of FIG. 1A, a cosmetic surgeon may prescribe a sedating medication, such as, but not limited to, AMBIEN (or another equivalent of AMBIEN) to help alleviate any anxiety that a patient may have prior to surgery. It may be preferable that the AMBIEN is provided in oral form, including as a tablet or capsule, although any acceptable form for its medicinal administration as known in the art may be used. It is a desired effect of one or more embodiments of the method provided herein to standardize the process of providing oral sedatives to a patient prior to surgery, including by providing an oral sedative the night before the surgery is to occur. This method may provide greater attention to the psychological condition of the patient prior to the surgery, instead of only focusing on the patient's physical condition as is common with many existing medical practices associated with cosmetic surgery.

On the day of the surgery, a number of steps may occur. At step 108, the cosmetic surgeon may provide a prescription for a first dosage of oxycodone and a first dosage of promethazine to be taken by the patient prior to the arrival of the patient at the surgical facility. Oxycodone is an opioid that is known for being an effective painkiller. In fact, it is a moderately potent analgesic (relieves pain) that may be used to relieve moderate to severe pain. Promethazine is a type of drug or medication that may be used to alleviate nausea for the patient. In one exemplary embodiment, a preferred dosage for a first dosage of oxycodone may be 10 mg of oxycodone and a preferred dosage for a first dosage of promethazine may be 25 mg of promethazine. The combination of the oxycodone and promethazine as shown in step 108 to be taken by the patient prior to arrival at the surgical center allows the patient to begin to feel the effects of the oxycodone at an earlier stage. Oxycodone may require anywhere from 30 to 120 minutes to take effect on a patient.

As shown at step 110 in FIG. 1A, a cosmetic surgeon will want to verify that the patient has taken at least the antibiotic medication, first dosage of oxycodone, and first dosage of promethazine prior to the patient's arrival at the surgical facility. It may be the case that for various reasons the patient does not take all of the above medications, including that the patient forgets to follow the recommended course of medications or has not filled their prescription. In this case, the process as provided herein is flexible to accommodate such a scenario. As shown in step 112, the operating physician should have the necessary medications at the surgical facility and may catch the patient up on the recommended course of medications by providing a patient with their necessary course of antibiotic medications, the oxycodone, and promethazine. It may even be preferable for the operating physician to provide a double dosage of antibiotic medication. Thus, the physician is able to accommodate the variation as noted in step 112. If the patient has taken the medications prior to arrival at the surgical center, in accordance with steps 104-108, then the process may proceed to step 114, as shown in FIG. 1A.

Advantageously, a patient is not required to fast for an extended period of time prior to taking these medications. At most, the patient may be recommended to cease eating or drinking no more than 2 to 3 hours prior to surgery. This is because the process shown in FIGS. 1A-1B is implemented in a novel and unique manner without the need for administering general anesthesia and without the use of an IV catheter for sedation of the patient during the cosmetic surgical procedure. Rather, the combination of medications provided in steps 104-108, and also in step 114 as further described below are successful in providing the necessary relief from pain, anxiety, or memory formation for a patient and replace the conventional use of general anesthesia or IV sedation for cosmetic surgical procedures. It is common procedure that when general anesthesia or IV sedation is used during surgery, a patient may be prevented from taking anything by mouth (e.g. "Nothing by mouth" or "Nothing PO") for anywhere from 4 hours to 12 hours prior to surgery. Thus, a patient may be required to fast and abstain from any food or drink, other than water. Further, a patient may be forbidden by their physician from taking their standard medications, such as diabetic medications or other medications to treat any conditions a patient may have. Fasting represents a change for a patient from their normal routine and can contribute to their psychological anxiety and sense of discomfort. It may be of particular importance for the patient to be able to have breakfast and to take basic medications and/or supplements. Beneficially, if a cosmetic surgeon follows the non-limiting steps for treatment of a patient prior to a cosmetic surgical procedure, the patient may be allowed to eat or drink most of their normal foods and drink up until about 2 hours prior to undergoing surgery. Further, they should not have a problem taking any of their standard medications, such as diabetes medications, unless there are special circumstances determined by the physician during the preoperative evaluation provided for in step 104 as described above.

Continuing to step 114, a cosmetic surgeon may provide a dosage of lorazepam, another AMBIEN, and a dosage of hydroxyzine for the patient. The dosage of lorazepam, AMBIEN, and hydroxyzine may be provided at the surgical facility. Lorazepam is a type of benzodiazepine medication that has a number of effects on a patient. Lorazepam has a high relative potency and lasting effects that may range anywhere from 10-20 hours on a patient. Lorazepam may further interfere with memory formation and ultimately may be useful for sedation of the patient prior to undergoing cosmetic surgery. Hydroxyzine is a type of medication that reduces activity in the central nervous system, and is used as a sedative for relieving tension and anxiety. In a preferred, non-limiting embodiment, it may be preferable to prescribe a dosage of between 2 mg to 6 mg of lorazepam for the patient, a dosage of 20 mg of AMBIEN, and a dosage of 25 mg of hydroxyzine.

There are many advantages for using lorazepam at step 114 in the process outlined in FIG. 1A. For example, lorazepam is considered a moderate anti-anxiety benzodiazepine that beneficially complements the oxycodone and promethazine. Further, the lorazepam may cause the patient not to have a full memory of the cosmetic surgical procedure, but rather have a sense of amnesia. Accordingly, it is likely that the patient may remember portions of the surgery but not the entire process. An initial amount of time may be provided for the patient to relax at a location in the surgical facility and for the medications to take effect.

After a minimum duration of time following the consumption by the patient of the medications listed in steps 106-114, the cosmetic physician may provide an assessment whether the combination of medications provided in steps 106-114 have produced the desired effects on the patient (step 116), or whether additional sedating medication may be needed (step 118). In particular, the operating physician at step 116 assesses the level of sedation, anxiety level, and threshold level of pain or pain tolerance of the patient after having received the combination of medications listed in steps 106-114. In order to make a qualified evaluation of a patient's level of anxiety, sedation, and threshold level of pain at step 116, it is preferable that the operating physician have experience with and knowledge of pain management, including chronic and acute pain management. The operating physician may preferably also be well-trained in administration of anxiety medications, such as oxycodone and sedatives, such as AMBIEN, as well as the use of medications such as lorazepam and hydroxyzine. It should be of paramount importance for a cosmetic surgeon practicing the process shown in FIGS. 1A-1B to use these medications in a safe and effective manner.

To be sure that the combination of medications has taken effect on the patient, an operating physician should pay particular attention to the alertness level and the demeanor of a patient. Notably, the patient may exhibit certain telling symptoms, such as a slight to severe slurring of their speech or seeming very drowsy and exhibiting a desire to sleep. For the majority of people, the combination of medications listed above should be fast acting and quickly provide sedation from the oral sedatives, and also a relief from anxiety. However, there are individuals that may be more tolerant of medicines such as oxycodone, lorazepam, and AMBIEN. This may be due to a number of factors. A patient may have a history of taking such medications frequently and thus may have a built-up tolerance to the effects of analgesics, such as oxycodone, and anxiolytics, such as AMBIEN and/or hydroxyzine. Further, it may be common for a patient to use narcotics, including marijuana, or to consume alcohol regularly, and have adapted their body to such treatment. Alternatively, or additionally, the patient may be so anxious that they need additional sedation and relief. Notably, there may be a myriad of reasons that a patient may have a higher tolerance level and thus the patient may not be at an optimal level of sedation at step 116. If the operating physician (or other skilled person in the art), assesses that additional medication may be needed (e.g. step 118), then a second dosage of oxycodone and promethazine may be provided, as shown at step 120. In one exemplary, non-limiting embodiment, a dosage of 10 mg of oxycodone and 25 mg promethazine may be provided at step 120.

At step 118, the operating physician determines that the patient is sufficiently sedated and will not feel pain during surgery. Thus, the operating physician determines that the patient is ready to proceed to surgery and may direct the patient to the operating room as shown at step 122 in FIG. 1A. All the standard routines for monitoring the safety and comfort level of the patient should be adhered to, including monitoring the vital signs of the patient. Thus, the heart rate, blood pressure, temperature, and all of the standard monitoring procedures for performing cosmetic surgery should be followed in implementation of the process shown in FIGS. 1A-1B.

Further, it is noted that at step 122, the patient may still be ambulatory and able to walk to the operating room. Some patients may be too sedated and may need to be transported to the operating room on a gurney to the operating room. However, a large percentage of the patients who receive the combination of medications listed above will be sedated but not automatically put to sleep.

Prior to surgery, an operating physician will have prepared a solution for tumescent anesthesia in order to perform the cosmetic surgical procedure using the tumescent technique. The tumescent technique using tumescent anesthesia may involve the injection of medium to large volumes of diluted local anesthetic such as lidocaine into subcutaneous fat, obtaining swelling and firmness (tumescence) of the surgical area and also creating regional anesthesia of the skin and subcutaneous tissue that allows cutaneous surgery without pain. As previously described, in cutaneous surgery, there are a number of advantages to using tumescent anesthesia, including anaesthetization of large areas of body surface, low incidence of bleeding, and prolonged postoperative analgesia which further helps reduce discomfort and pain post operation for the patient. It may also facilitate surgical dissection and reduce post-operative swelling and bruising.

A solution of tumescent anesthesia in accordance with one or more embodiments may be generally described as an anesthetizing salt solution that includes lidocaine, epinephrine, and sodium bicarbonate. In one or more embodiments, a cosmetic surgeon may provide a first round of numbing during the infiltration of the targeted areas with tumescent anesthesia (ex. step 124 in FIG. 1B) and then also provide a second round of numbing for a patient to ensure that a targeted area on which a cosmetic surgical procedure will be performed is sufficiently anesthetized. For a first round of numbing using the tumescent anesthesia (e.g. via infiltration), a process for making a concentrated solution of tumescent anesthesia using a high amount of lidocaine may include diluting 50 cubic centimeters (cc) of 2% lidocaine in 1 liter of normal saline (0.9% saline), with 10 cubic centimeters of 8.4% sodium bicarbonate, and then diluting 1 cubic centimeter of epinephrine in the solution. As known in the art, normal saline is an isotonic solution that is a sterile mixture of salt and water.

Subsequently, a second round of numbing may be provided to ensure additional anesthesia is provided to a targeted area. In a second round of numbing, the tumescent anesthesia may include diluting 25 cubic centimeters of 2% lidocaine in 1 liter of normal saline with 10 cubic centimeters of 8.4% sodium bicarbonate, and then diluting 1 cubic centimeter of epinephrine in the solution.

For specific body parts, such as the face and breast, a super concentrated solution of tumescent anesthesia may be provided in a first round of numbing. In one embodiment, a super concentrated solution of tumescent anesthesia to be used for cosmetic surgical procedures for the face and breast may be may be achieved by dilution of 75 cubic centimeters of 2% lidocaine in 1 liter of normal saline, with 10 cubic centimeters of 8.4% sodium bicarbonate, and then diluting 3 cubic centimeters of epinephrine in the solution. This may be followed up with a second round of numbing as stated above. Notably, the amount of epinephrine may be increased by about three times that of other body parts for face lifts or breast augmentation procedures, including breast implants.

It is noted that the tumescent anesthesia solution may be prepared using any preferred technique known in the art for tumescence anesthesia. In one embodiment, it may be preferred for the tumescent local anesthesia to include between about 35 mg/kg to 55 mg/kg of body weight of lidocaine. Further, in another embodiment, it may be more preferable for the tumescent local anesthesia to include between about 45-55 mg/kg of body weight of lidocaine.

The tumescent anesthetizing solution just described above has a higher concentration of lidocaine than is conventionally used by most practitioners. The resulting amount of lidocaine based on the formulations offered above may place the lidocaine level from about 45 mg/kg of body weight to about 55 mg/kg of body weight, which is a novel and useful improvement offered in the present description. Conventional procedures usually utilize a level of lidocaine no higher than 35 mg/kg of body weight, which has been traditionally endorsed by many physicians, including Dr. Klein, who is considered a renowned inventor of the procedures. The package insert labeling approved by the United States Food and Drug Administration (FDA) for lidocaine with epinephrine, in fact, states that the recommended maximal dosage is 7 mg/kg for infiltration local anesthesia. It has been noted before in many articles that this dosage is antiquated and invalid, because the FDA has no data to support this claim of 7 mg/kg as the maximum dosage limit. It is reputed that the 7 mg/kg dosage limit was originally established in 1948 for epidural anesthesia and has not been updated or changed over the years despite advances in understanding the use of tumescent solutions of lidocaine and epinephrine.

Nevertheless, multiple implementations of the process shown in FIGS. 1A-1B and described above have shown that this amount of lidocaine does not usually have any unwanted negative reactions on a patient, nor is it common for lidocaine toxicity to occur, despite the conventional assumption that these levels of lidocaine may be toxic. Notably, recent clinical evidence shows the success of and lack of harm to the patient from using lidocaine mixed with epinephrine in the anesthetizing solution at the 45 mg/kg-55 mg/kg level.

There have been several studies and publications that indicate that lidocaine toxicity is not of significant concern even with higher levels of lidocaine, because some of the anesthetic is immediately suctioned after infiltration, which prevents systemic absorption. Further, the diluted concentrations allow the anesthetic to be isolated in the subdermal tissue of the skin, which indicates that the lidocaine is absorbed slowly and should not overwhelm the hepatic breakdown rate.

With respect to the use of the epinephrine in the tumescent solution, its use is also well documented. The use of epinephrine in the tumescent local anesthesia offers a number of desirable results during surgical procedures, including cosmetic surgical procedures as noted above. Epinephrine is a vasoconstrictor, which is an agent that causes narrowing of an opening of a blood vessel. As such, the epinephrine assists in significant minimization of any blood loss that occurs during liposuction and other cosmetic surgical procedures, especially when compared with methodologies that do not use tumescent anesthesia or epinephrine.

Because the tumescent solution is so effective, it is recommended in the present description that tumescent anesthesia be utilized for any cosmetic surgical procedure (as noted at step 126). Many physicians associate tumescent anesthesia and infiltration as being used only with liposuction procedures. However, it is a discovery of the inventor that tumescent local anesthesia is extremely effective with a variety of cosmetic surgical procedures, including, but not limited to, liposuction, fat grafting, tummy tucks, arm lifts, face lifts, breast lifts, breast implants, breast reductions, and other cosmetic surgical procedures listed above.

Tumescent infiltration, which occurs at step 124 in the process shown in FIG. 1B, is a highly useful tool in all of these examples of cutaneous surgery. To infiltrate a targeted area of the body, the operating cosmetic surgeon may use a thin needle, known in the art as a cannula (or microcannulas may be used), to inject the targeted area or areas of the body with the tumescent anesthesia. Because lidocaine is very fast acting, the tumescent anesthesia should begin numbing and anesthetizing the targeted area very quickly. For example, within 1 to 5 minutes, it has been shown that the tumescent anesthesia should take effect, although additional time may be provided to ensure the anesthetizing solution is infused in the targeted area. Conventional procedures may prescribe waiting at least thirty minutes after the infiltration process for the tumescent anesthesia to be optimal, however, this may not be necessary as experience has shown that the solution is effective in a much quicker time frame.

Once the minimum duration of time has passed for the tumescent solution to infiltrate in the targeted area of the body, the cosmetic surgeon may perform the cosmetic surgical procedure with the continuous use of the anesthetizing solution as shown in step 126. As described above, the anesthetizing solution should preferably contain a higher amount of lidocaine that may range from about 45 mg/kg to 55 mg/kg.

In one or more embodiments, the use of the tumescent anesthesia may be a method of administration of local anesthesia and avoids the need for either general anesthesia or IV sedation. Nevertheless, it is noted that there may be some cases for particular patients who may have a higher level of anxiety, low tolerance for pain, or who have requested that the operating physician further use IV sedation as needed to provide additional relief from sensation and awareness of the surgery for a patient in conjunction with all of the steps provided in the process shown in FIGS. 1A-1B. As such, in some applications, where it is safe to do so, the operating physician may also provide IV sedation of lorazepam in conjunction with the tumescent anesthesia and after administration of the oral sedatives listed above.

In one or more embodiments, after the surgery, a cosmetic surgeon may optionally provide a patient with one or more reversing agents as shown in step 128. Even though a patient after the surgery may feel happy and comfortable from the tumescent anesthesia, it may be challenging for caregivers to take care of and help the patient be safely and efficiently discharged when the patient is sleepy and groggy. If a patient is more alert after the surgery, the patient may be more cooperative with caregivers. In order to make the sleepy and groggy patient to be more alert, the effects of benzodiazepine and oxycodone may be reversed after the surgery. For example, about 1 ml of 0.5 mg/5 ml flumazenil solution may be administered through intramuscular (IM) injection on the deltoid, outer hip, or gluteal region, to reverse the effect of benzodiazepine, such as lorazepam. Likewise, in order to reverse the effect of oxycodone, about 1 ml of 0.4 mg/ml naloxone solution may be administered through IM injection on the deltoid, outer hip, or gluteal region.

Advantages of the combination of drugs used in one or more embodiments in the present description is that the patient remains comfortable, relaxed, and free of pain during cosmetic surgery procedures. The process shown in FIGS. 1A-1B further alleviates anxiety of the patient from the day before the surgery is to take place and continues into the day of the surgery. The attention to both the physical and psychological state of a patient for the entire surgical process (perioperative) is a particular benefit offered by one or more methods described herein. Additionally, a significant benefit of the above-identified method of administering oral sedation in combination with tumescent anesthesia has the desirable effect of dramatically decreasing any bleeding or the effects of excessive blood loss from surgery. Accordingly, as a result of the process shown in FIGS. 1A-1B, there are no drains, no blood transfusions, and no fatigue to the patient due to the blood loss upon having one or more cosmetic surgery procedures performed.

Notably, the ability to successfully and effectively perform cosmetic surgery without having to use general anesthesia or IV sedation is also of significant benefit for the patient. During general anesthesia, a patient is rendered unconscious and unable to breathe on his or her own and must be attached to a machine to breathe on their behalf. Further, general anesthesia includes all of the notable risks described above such as the potential for heart attacks and/or cardiac arrest, lung infections and/or pneumonia, pulmonary embolism, or renal failure/insufficiency to name a few. Similarly, the use of IV sedation for anesthesia presents its own potential risks of complications which include, respiratory depression, cardiac depression, stress to the patient from putting in the IV, an infiltrated IV, thrombosis of the vein that the IV is located in, as well as thrombophlebitis, without limitation thereto. In contrast to the above, a significant advantage to the process identified in FIGS. 1A-1B and not needing to utilize general anesthesia or IV sedation is that supplemental oxygen is not necessary for the patient during the cosmetic surgical procedure as the oxygen saturation for the patient is usually at least 90%. Clinical trials have shown that, in fact, the oxygen range is between 95%-99%. This is a great benefit to the patient because the presence of supplemental oxygen presents flammability issues, and there have been actual incidents of spontaneous fires occurring due to the use of supplemental oxygen in surgery, which beneficially may be avoided using the process identified in FIGS. 1A-1B.

Further, when in general anesthesia and/or deep sedation, the patient has no awareness or cognitive capability. On the other hand, the process provided in steps 102-128 in FIGS. 1A-1B allows the patient to have some level of consciousness during the cosmetic surgical procedure. Many patients after receiving the combinations of medications listed above are still able to respond to verbal cues and commands from an operating physician or other medical care provider at the surgical center, and are able to also express and share their thoughts and feelings during the cosmetic surgical procedure. While this approach may seem counterintuitive to many conventional procedures that proscribe to over use of general anesthesia, it has been shown in multiple implementations to be satisfactory, safe, and provide desirable outcomes for the patient and the cosmetic surgeon.

Further, an additional advantage of one or more techniques used herein is that physicians/surgeons can apply local anesthetics as described herein without absolutely requiring the presence of an anesthesiologist. Only certified anesthesiologists can administer general anesthesia, as well as epidural and spinal anesthesia. Therefore, by implementing one or more steps of the method for administering anesthesia, the overall cost of the cosmetic surgical procedure may be reduced as it is not necessary to have on staff and/or in the operating room a certified anesthesiologist. Nevertheless, as previously emphasized, it is of paramount importance that the cosmetic surgeon administering the process in FIGS. 1A-1B have adequate training and experience in the use of these techniques and combinations of medications. Further, it may not be preferable for the above-listed combination of medications and/or tumescent anesthesia to be utilized with anyone under the age of 18 years old.

Figure 2:
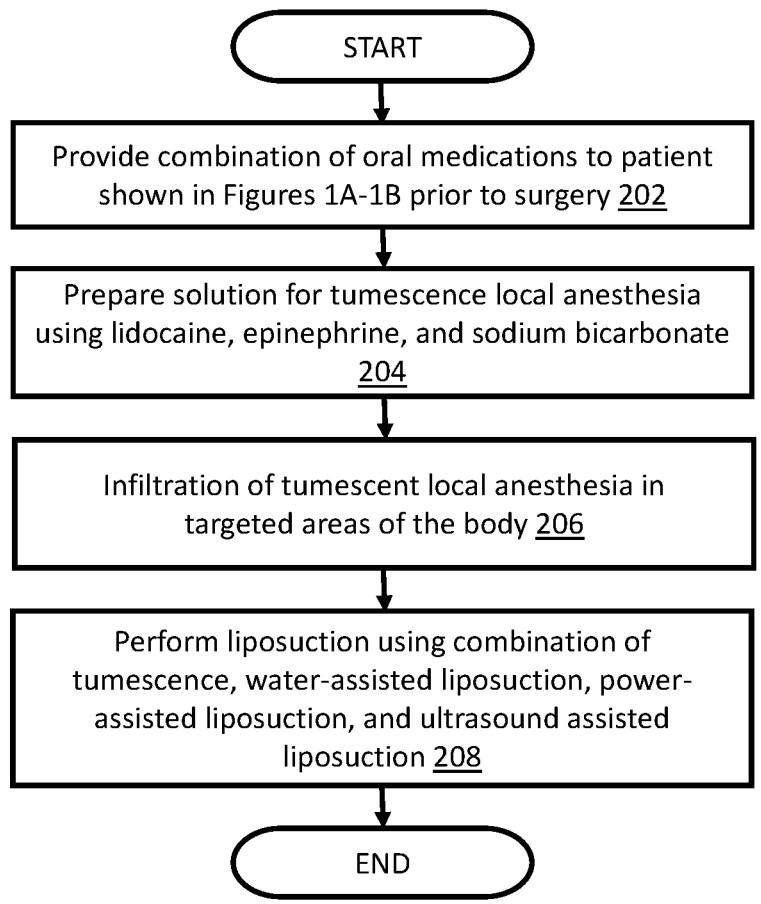
FIG. 2 illustrates a flowchart for a method of performing liposuction in accordance with an illustrative embodiment.

Turning to FIG. 2, FIG. 2 shows a flowchart for an exemplary novel and non-obvious method for performing liposuction that encompasses a variety of techniques. Liposuction is a highly sought after surgical procedure that reduces body fat by removing localized fat deposits. Liposuction may be particularly helpful in removing stubborn fat deposits that are resistant to diet and exercise. Individuals often choose to have liposuction performed in various areas of the body, including the abdomen, the thighs, arms, and anywhere else a patient desires to reduce the amount of fat or appearance of lumpiness beneath the skin. It is important to note that, although FIG. 2 shows an exemplary method for performing liposuction utilizing the combination of oral sedation and tumescent anesthesia described above with FIGS. 1A-1B, the combination of oral sedation and tumescent anesthesia described above is applicable to any cosmetic surgical procedures known to a person having ordinary skill in the art including, but not limited to, breast enhancement, facial surgery, body contouring, and/or skin rejuvenation.

Prior to performing a liposuction procedure, as noted in step 202 in FIG. 2, it may be desirable for a cosmetic surgeon to utilize any or all of steps previously described and shown in FIGS. 1A-1B. In particular, steps 102-124 in FIG. 1A offer numerous advantages and improvements over conventional cosmetic surgical procedures.

At step 204 in FIG. 2, the tumescent local anesthetic solution has been prepared for use during the liposuction procedure, whereby the tumescent anesthetic solution is based on the combination of lidocaine, epinephrine, and sodium bicarbonate as previously described. Further, in step 206, the cosmetic surgeon may utilize a cannula (of any preferred size or type) for injection and infiltration of the tumescent solution in the targeted areas of the body where the liposuction procedure is to occur. Beneficially, the patient may be adequately sedated and the lidocaine in the anesthetizing solution is fast acting to quickly numb the targeted area of the body and to alleviate any pain that would otherwise be sensed by the patient. Ultimately, the anesthetizing solution is infused throughout the targeted area where the liposuction is to occur.

Additionally, in order to provide a smoother and firmer appearance to the skin after the liposuction procedure, a number of techniques may be utilized that are not conventionally utilized. As shown in step 208, in a preferred embodiment of the process shown in FIG. 2, liposuction may be performed using a combination of tumescent anesthesia, as well as water assisted liposuction, power assisted liposuction, and ultrasound assisted liposuction. Most preferably, a cosmetic surgeon will utilize all four techniques, but it may be sufficient that a cosmetic surgeon at least utilizes the tumescence anesthesia in combination with water assisted liposuction and then either the power assisted liposuction or the ultrasound assisted liposuction as desired by the cosmetic surgeon.

Water-assisted liposuction is a liposuction technique that uses water to help loosen fat cells from connective tissue and then gently remove them. The water-assisted liposuction techniques often are implemented using the BODY JET system (trademark), which utilizes a gentle jet of water to simultaneously dislodge and remove fat from the body, while sparing blood vessels, nerves, and surrounding tissue. There are several advantages to this process, including that it is safe, effective, and gentler than traditional methods of liposuction. Further, water assisted liposuction spares surrounding tissue, minimizes trauma for patient, minimizes bleeding, bruising and swelling, and minimizes patient risk.

The power assisted liposuction is a method of performing liposuction that utilizes a vibrating tool that speeds up the breakdown of fat. Power assisted liposuction devices use power supplied by an electric motor or compressed air to an attached cannula to produce either a rapid in-and-out movement or a spinning rotation of the attached cannula. The power assisted cannula rotates based on predetermined angle and speed settings, allowing physicians to quickly remove fatty tissue all the way around the cannula, rather than just above or below the orifice.

Ultrasound assisted liposuction (also known as ultrasonic assisted liposuction) is a modified liposuction technique that delivers ultrasonic energy to subcutaneous fat. During ultrasonic liposuction, fat removal is initiated by sound waves produced by a generator. The ultrasonic waves are transmitted to a thin, vacuum-like cannula. When the cannula comes into contact with the fat cells, they quickly liquefy, and are easily vacuumed out. Some ultrasonic liposuction techniques do not destroy the fat cells and the removed fat can be used for fat transfer operations. It is noted that the cosmetic surgeon may need additional training in ultrasound assisted liposuction. Because a large amount of heat is created during ultrasonic liposuction, there may be some risk of burns, blistering, and scarring, but an experienced surgeon will know how to avoid these problems. Further, it is important to be aware of a possibility of a seroma developing, which occurs when the body tries to fill the void created by fat removal by producing excess fluid. This fluid must be removed continuously with a syringe until the cavity has closed.

The above procedures may be preferable to using laser assisted liposuction. Laser assisted liposuction is another existing liposuction technique that utilizes laser energy to heat the fat to be removed. The disadvantage of laser assisted liposuction is that it also destroys the fat cells meaning that the destroyed fat tissue cannot be repurposed later for fat transfer to another part of the body. Accordingly, because the water assisted liposuction, power assisted liposuction, and some ultrasound assisted liposuction techniques do not destroy the fat tissue, but rather just remove them, it is feasible for a cosmetic surgeon to utilize the removed fat under these techniques for later fat grafting procedures.

In terms of an order for performing the liposuction, it may be preferable to first infuse the targeted area with tumescent anesthesia (as described in step 206), followed by the use of the water assisted liposuction. Subsequently, a cosmetic surgeon may proceed with utilizing the power assisted liposuction, followed by the ultrasound assisted liposuction. However, to the surgeon may determine whether it may be more advantageous to follow the water assisted liposuction with either the power assisted liposuction first and then the ultrasound assisted liposuction next or whether to reverse that order depending on the characteristics of the fat tissue. A cosmetic surgeon is likely not to really know how fibrous the fat tissue is until after beginning with the liposuction procedure and being able to view the fat tissue to be removed.

It is a novel aspect of the present description that when a patient requests a liposuction procedure at an initial consultation, the cosmetic surgeon may recommend and ultimately utilize tumescence in combination with water assisted liposuction, power assisted liposuction, and ultrasound assisted liposuction. The conventional wisdom is that a cosmetic surgeon will utilize at most only one or two of these techniques. Thus, surgical facilities may offer the use of tumescent anesthesia with liposuction, but not utilize water assisted liposuction, power assisted liposuction, or ultra sound assisted liposuction. However, the benefit of utilizing all of the above techniques is greater precision contouring, more effective and efficient removal of fat deposits, particularly stubborn fat deposits, and tightening of the skin, which means better results for the patient and value for the cost of cosmetic surgery.

Nevertheless, it is noted that in some alternative embodiments, it may be sufficient for a cosmetic surgeon to utilize tumescent liposuction with two of the three additional techniques. For example, it may be effective to utilize the tumescent anesthesia with only the water assisted liposuction and/or power assisted liposuction or ultra sound assisted liposuction.

By combining all of the above techniques for performing liposuction, the cosmetic surgeon may offer outstanding results with minimal risk to the patient, and dramatically less bleeding, which advantageously means that there is no need for drains, no blood transfusions, and no fatigue for the patient due to blood loss.

A significant improvement and advantage in the use of the tumescent anesthesia with the liposuction and the many cosmetic surgical procedures listed herein is less pain and discomfort to the patient post-operation as compared to traditional techniques. Traditional liposuction techniques require patients to be in the hospital for days. Further, cosmetic surgical procedures, such as tummy tucks or breast lifts or implants had the effect of causing a patient to experience considerable pain so that they could not stand normally or independently without aid. After multiple experiments with the techniques described above, the patients are able to stand and do not experience the same amount of pain and discomfort as they would otherwise. In fact, most of the patients who undergo these techniques are still able to walk after surgery (with some exceptions depending on the nature of the surgery) and may need much less downtime including time away from work or reduced ability to move and operate in their daily lives, because the procedures have a gentler, more sedating and less stressful overall effect on their bodies. Moreover, these advantages may be further increased by administering reversing agents after the surgery. In addition, the use of the water assisted liposuction, power assisted liposuction, and ultrasound assisted liposuction contributes to much less bruising and swelling, so a patient may only need to be wearing the well-known compression garments for a shorter period of time. Further, the cosmetic surgeon is able to provide an enhanced method for removing fat and body contouring to provide the look that the patient desires.

Accordingly, the processes provided in the present description provide an effective, safe, and reproducible process using a combination of oral sedation and tumescence anesthesia, having at least 45 mg/kg-55 mg/kg of lidocaine in most applications, that may be used to perform a variety of cosmetic surgical procedures without the need for general anesthesia or IV sedation.

While the present invention has been related in terms of the foregoing embodiments, those skilled in the art will recognize that the invention is not limited to the embodiments described. The present invention may be practiced with modification and alteration within the spirit and scope of the appended claims. Thus, the description is to be regarded as illustrative instead of restrictive on the present invention.

The invention claimed is:

1. A method for anesthetizing a patient undergoing a cosmetic surgical procedure comprising:
  administering orally an antibiotic medication at least from about 12 hours to about 24 hours prior to the cosmetic surgical procedure;

administering orally a first dosage of oxycodone and a first dosage of promethazine to be taken by the patient prior to arrival at a surgical facility where the cosmetic surgical procedure is to occur; and administering orally a dosage of lorazepam, a dosage of zolpidem, and a dosage of hydroxyzine prior to the cosmetic surgical procedure.

2. The method of claim 1, wherein the method is performed without using general anesthesia and without using intravenous (IV) sedation.

3. The method of claim 1, wherein the first dosage of the oxycodone is from about 10 mg and the first dosage of promethazine is from about 25 mg.

4. The method of claim 1, wherein the dosage of the lorazepam is from about 2 mg to about 6 mg.

5. The method of claim 1, wherein the dosage of the zolpidem is from about 20 mg.

6. The method of claim 1, wherein the dosage of the hydroxyzine is from about 25 mg.

7. The method of claim 1, further comprising: performing an assessment of a sedation level, an anxiety level, and a threshold level of pain tolerance of the patient to determine whether the patient is ready to undergo the cosmetic surgical procedure.

8. The method of claim 7, further comprising: if the sedation level, the anxiety level, or the threshold level of pain tolerance is not sufficient for the patient to undergo the cosmetic surgical procedure, providing a second dosage of oxycodone and a second dosage of promethazine to the patient.

9. The method of claim 1, further comprising: directing the patient to an operating room for the cosmetic surgical procedure.

10. The method of claim 1, further comprising: performing tumescent local anesthesia during the cosmetic surgical procedure.

11. The method of claim 10, wherein the performing tumescent local anesthesia further comprises:
preparing an anesthetizing solution comprising lidocaine, epinephrine, and sodium bicarbonate; and
infiltrating the anesthetizing solution in a targeted area of the patient.

12. The method of claim 11, wherein the anesthetizing solution comprises: solution of from about 50 cc of 2% lidocaine, 10 cc of 8.4% sodium bicarbonate, and 1 cc of epinephrine in 1 liter of normal saline.

13. The method of claim 11, wherein the anesthetizing solution comprises: solution of from about 75 cc of 2% lidocaine, 10 cc of 8.4% sodium bicarbonate, and 3 cc of epinephrine in 1 liter of normal saline.

14. The method of claim 11, wherein the lidocaine in the anesthetizing solution infiltrated in the targeted area of the patient is from between about 45-55 milligram per kilogram of the patient's body weight.

15. The method of claim 10, further comprising: providing one or more reversing agents to the patient after the cosmetic surgical procedure.

16. The method of claim 15, wherein the one or more reversing agents comprises flumazenil.

17. The method of claim 15, wherein the one or more reversing agents comprises naloxone.

18. A method for performing liposuction for a patient, comprising:
administering orally a combination of medications for relieving the pain and anxiety of a patient prior to a cosmetic surgical procedure, wherein the combination of the medications comprises:
a first dosage of oxycodone and promethazine,
a dosage of lorazepam,
a dosage of zolpidem, and
a dosage of hydroxyzine;
providing tumescent local anesthesia for the patient; and
performing the cosmetic surgical procedure, wherein the cosmetic surgical procedure further comprises a combination of one or more of water-assisted liposuction, power-assisted liposuction, and ultrasound-assisted liposuction.

19. The method of claim 18, wherein providing tumescent local anesthesia further comprises:
preparing an anesthetizing solution comprising lidocaine, epinephrine, and sodium bicarbonate; and
injecting the anesthetizing solution in a target area of the patient during the cosmetic surgical procedure.

20. The method of claim 18, further comprising: providing one or more reversing agents to the patient after performing the cosmetic surgical procedure.

* * * * *